(12) United States Patent
Hua et al.

(10) Patent No.: US 11,882,797 B2
(45) Date of Patent: Jan. 30, 2024

(54) AUTOMATIC DETECTION AND RECOVERY DEVICE FOR RESIDUAL AGRICULTURAL MULCH FILM, AND METHOD OF USING SAID DEVICE

(71) Applicant: NANTONG UNIVERSITY, Nantong (CN)

(72) Inventors: Liang Hua, Nantong (CN); Zeguang Zhang, Nantong (CN); Jiahan You, Nantong (CN); Yisheng Huang, Nantong (CN); Ping Lu, Nantong (CN)

(73) Assignee: NANTONG UNIVERSITY, Nantong (CN)

( * ) Notice: Subject to any disclaimer, the term of this patent is extended or adjusted under 35 U.S.C. 154(b) by 0 days.

(21) Appl. No.: 17/052,496

(22) PCT Filed: Feb. 24, 2020

(86) PCT No.: PCT/CN2020/076323
§ 371 (c)(1),
(2) Date: Nov. 2, 2020

(87) PCT Pub. No.: WO2020/207128
PCT Pub. Date: Oct. 15, 2020

(65) Prior Publication Data
US 2022/0386540 A1  Dec. 8, 2022

(51) Int. Cl.
*A01G 13/02* (2006.01)
*G01N 33/24* (2006.01)
(Continued)

(52) U.S. Cl.
CPC ............ *A01G 13/0287* (2013.01); *B07C 5/02* (2013.01); *B07C 5/342* (2013.01); *B07C 5/362* (2013.01); *B25J 11/00* (2013.01); *G01N 21/359* (2013.01); *G01N 21/3554* (2013.01); *G01N 33/246* (2013.01); *A01G 2013/0218* (2013.01);
(Continued)

(58) Field of Classification Search
CPC ....... A01G 13/0287; A01G 2013/0218; G01N 33/246; G01N 2033/245; G01N 21/3554; G01N 21/359; B07C 5/02; B07C 5/342; B07C 5/362; B07C 2501/0063; B25J 5/007; B25J 19/023; B25J 11/00; A01B 43/00
See application file for complete search history.

(56) References Cited

U.S. PATENT DOCUMENTS 10,796,275 B1 * 10/2020 Wilkins ............... G06Q 10/087
2014/0303814 A1 * 10/2014 Burema et al. ......... A01C 21/00
901/1
(Continued)

*Primary Examiner* — Thomas B Will
*Assistant Examiner* — Joel F. Mitchell
(74) *Attorney, Agent, or Firm* — CBM PATENT CONSULTING, LLC

(57) ABSTRACT

An automatic detection and recovery device for residual agricultural mulch film, and a method of using the device, comprising a quadcopter, a wheeled robot (9), and a host computer (8); the quadcopter is provided with a controller (1), a near infrared water content analyzer, and a WiFi module that are used to measure water content in soil and communicate with the host computer; the wheeled robot (9) comprises a water sprinkling device (2), a soil grabbing device (3), a sifting device (4), a delivery device (5), a recognition device (6), and a sorting device (7).

5 Claims, 4 Drawing Sheets

Figure 1:
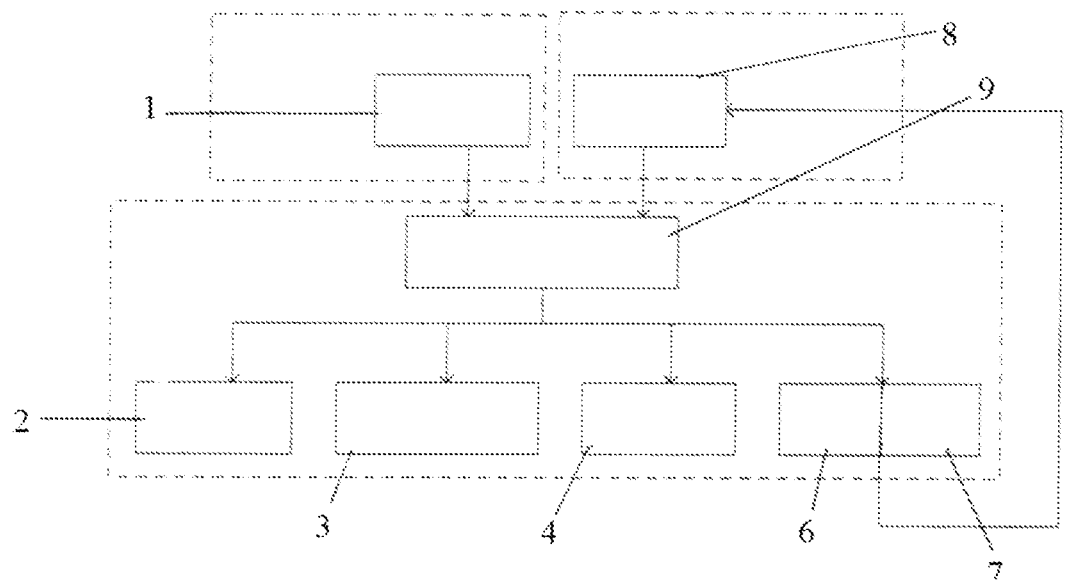

(51) Int. Cl.
  *B07C 5/02*       (2006.01)
  *B07C 5/342*      (2006.01)
  *B07C 5/36*       (2006.01)
  *B25J 11/00*      (2006.01)
  *G01N 21/3554*    (2014.01)
  *G01N 21/359*     (2014.01)

(52) U.S. Cl.
  CPC ............... *B07C 2501/0063* (2013.01); *G01N 2033/245* (2013.01)

(56) References Cited

U.S. PATENT DOCUMENTS

| | | | |
|---|---|---|---|
| 2017/0258005 A1* | 9/2017 | Cutter | A01B 79/005 |
| 2019/0102623 A1* | 4/2019 | Flood et al. | G05D 1/0022 |
| 2020/0015401 A1* | 1/2020 | Frei et al. | G06F 18/285 |
| 2021/0045379 A1* | 2/2021 | Grant | A01B 79/005 |
| 2021/0333259 A1* | 10/2021 | Andrejuk et al. | B64D 45/00 |
| 2022/0128504 A1* | 4/2022 | Gopalakrishnan et al. | G01N 27/223 |
| 2022/0151135 A1* | 5/2022 | Das et al. | G01C 21/3461 |
| 2023/0039403 A1* | 2/2023 | De Santo | B64C 39/024 |

* cited by examiner

AUTOMATIC DETECTION AND RECOVERY DEVICE FOR RESIDUAL AGRICULTURAL MULCH FILM, AND METHOD OF USING SAID DEVICE

TECHNICAL FIELD

The present invention relates to An automatic detection and recovery device for residual agricultural mulch film.

DESCRIPTION OF THE RELATED ART

With the development of agriculture, plastic film plays a more and more important role in agricultural production because it can promote the increase of farmers' income. However, with the increase of the use of plastic film, the cleaning of residual film is not timely, which not only damages the agricultural environment, but also seriously affects the agricultural production efficiency. Therefore, the residual film left in the cultivated land needs to be recycled, but most of the residual film in the soil is small flake, It is very difficult to detect and recover.

Technical Issues

The object of the invention is to provide An automatic detection and recovery device for residual agricultural mulch film.

An automatic detection and recovery device for residual agricultural mulch films comprises a quadcopter, a wheeled motor and a host computer. The quadcopter is provided with a controller, a near infrared water content analyzer and a WIFI module. The wheeled robot comprises a water sprinkling device, a soil grabbing device, a sifting device, a delivery device, a recognition device, and a sorting device.

The water sprinkling device comprises a water pump and a water tank that are disposed behind the wheeled robot, wherein water is pumped out of the water tank by the water pump and is uniformly sprinkled via mesh-like outlets, and when the wheeled robot advances in a field, water is ceaselessly and uniformly sprinkled on the surface of the field;

The soil grabbing device comprises a three-degree-of-freedom motor for joint control, wherein the three-degree-of-freedom motor includes two screw motors and a push-rod motor, a mechanical gripper is used for grabbing and is mounted at a front end of the push-rod motor that is perpendicular to the ground so that the mechanical gripper is able to stretch and retreat perpendicular to the ground, a tail end of the push-rod motor is vertically mounted on a nut of one screw motor that is parallel to the ground, and one end of a screw of this screw motor is vertically mounted on a nut of the other screw motor that parallel to the ground, so that the mechanical gripper is able to move horizontally parallel to the ground; the soil grabbing device is disposed in front of the wheeled robot, and when the wheeled robot travels to a point where a residual mulch film is present, the soil grabbing device grabs soil at this point;

The sifting device comprises a sifting barrel, a drying plate, a pushing device, a rotating device, a moving device and a recovery box, wherein the sifting barrel is divided into an upper sifting barrel and a lower sifting barrel that are both hollow semi-cylinders; small round holes are formed all over the cylindrical surface of the upper sifting barrel, a clamping groove is formed in the center of the outer surface of the upper sifting barrel, an upper opening of the upper sifting barrel is in the shape of a hollow semicircular ring, semicircular bumps are disposed at the center of two ends of the upper sifting barrel, and the upper sifting barrel is always located in the recovery box; the surface of the lower sifting barrel is completely sealed, semicircular bumps are disposed at the center of two ends of the lower sifting barrel, and the bump at one end of the lower sifting barrel is connected to the pushing device; soil grabbed by the soil grabbing device is placed into the lower sifting barrel; the drying plate is mounted on one side of the recovery box and is used for drying the grabbed soil; the pushing device is a push-rod motor, a motor base is mounted on the rotating device, and the head of a push rod is connected to the lower sifting barrel to deliver the lower sifting barrel into the recovery box or extract the lower sifting barrel from the recovery box; the rotating device comprises a rotating motor, a push-rod motor and a fixing ring, wherein the rotating motor is located on one side of the recovery box and is provided with a rotating shaft vertically connected to a base of the pushing device, the push-rod motor is located on the other side of the recovery box, the fixing ring is mounted at the head of a push rod of the push-rod motor, the rotating device locks the circular bump at one end of the sifting barrel through the fixing ring, and the rotating motor drives the lower sifting barrel to rotate, so that soil in the sifting barrel is sifted out via the small holes in the surface of the upper sifting barrel; the moving device comprises a fixing plate, a rotating motor, a push-rod motor and a semicircular clamping block, a tail end of the rotating motor is fixed to the fixing plate, a rotating shaft of the rotating motor is connected to a tail end of the push-rod motor, the semicircular clamping block is drilled at the head of a push rod and is able to rise or fall and rotate; the recovery box is a hollow cuboid, round notches are formed in two end faces of the recovery box to allow the sifting barrel to enter or come out, and the round notch in the upper end face of the recovery box allows the push rod of the push-rod motor of the moving device to move;

The delivery device comprises a shield plate and a conveying belt, wherein the conveying belt is used for conveying residues left after sifting, and the shield plate is used for flatly spreading the residues in the conveying process;

The recognition device adopts a monocular camera, shoots the residues in real time, and sends photos to the host computer, and the host computer processes image data and then selects out weak pixels to determine a residual mulch film;

The sorting device comprises a three-degree-of-freedom motor, a mechanical gripper and a residual film recovery box, wherein the motor and the mechanical gripper are mounted in a manner similar to the motor and mechanical gripper of the soil grabbing device, and the mechanical gripper moves to and grabs the determined residual mulch film, and then places the grabbed residual mulch film into the recovery box.

The drying plate of the sifting device is mounted on the shield plate of the delivery device.

The upper sifting barrel of the sifting device is always located in the recovery box, and the moving device rotates by 180° in the clamping groove above the sifting barrel through the semicircular clamping block and then rises to be separated from the upper sifting barrel.

A semi-ring is disposed at a joint of the lower sifting barrel of the sifting device and the pushing device and is used for fixing the whole sifting barrel after the lower sifting barrel is conveyed back into the recovery box and is aligned with the upper sifting barrel, such that the sifting barrel can rotate smoothly;

A method of using the automatic detection and recovery device for residual agricultural mulch films comprises the following steps:

S1: planning a motion path of the wheeled robot according to the geometrical shape and position of a detected field, and uniformly sprinkling water into the defected field by the wheeled robot;

S2: after the water infiltrates into soil by a certain depth, detecting the water content of the detected field by the quadcopter carrying the near infrared water content analyzer along the motion path of the wheeled robot, determining a point where the water content of soil is high as a point where a residual mulch film is present by judging the water content of the soil, and recording the coordinates of this point;

S3: transmitting, by the quadcopter, the coordinates of the point where the residual mulch film is present to the wheeled robot, enabling the wheeled robot to sequentially move to the point where the residual mulch film is present along a planned path, and grabbing a soil mixture at this point;

S4: drying the soil mixture by the wheeled robot, and separating and recovering soil through high-speed rotation after drying;

S5: flatly spreading residues left after the soil is sifted, recognizing the residual mulch film by means of machine vision, and grabbing the residual mulch film by the mechanical gripper.

Beneficial Effects

The invention can complete multiple functions of watering, grabbing, screening and sorting through a wheeled robot, uses a four-axis aircraft to carry near-infrared detection of water content, so as to judge the existence of residual film in soil; innovatively adopts the separation type screening bucket, which integrates two functions of soil collection and screening; uses machine vision to detect the residue mixed with residual film, and divides the brightness value of the image The invention has the advantages of simple structure, less workload, stable and reliable effect, and is suitable for popularization and use.

DESCRIPTION OF SEVERAL VIEWS OF THE ATTACHED DRAWINGS

Figure 2:
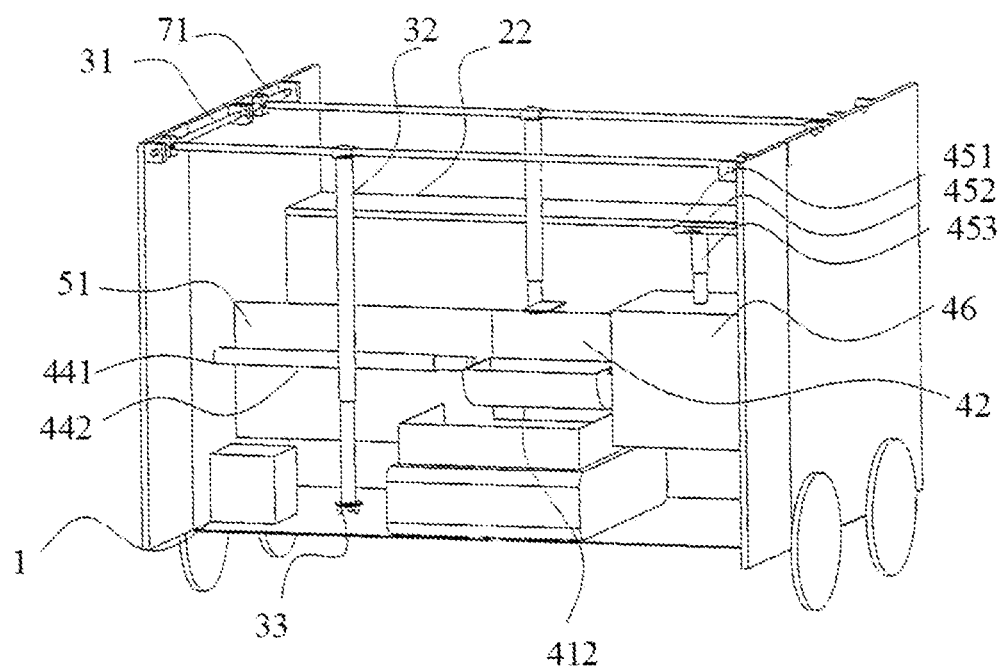
Figure 3:
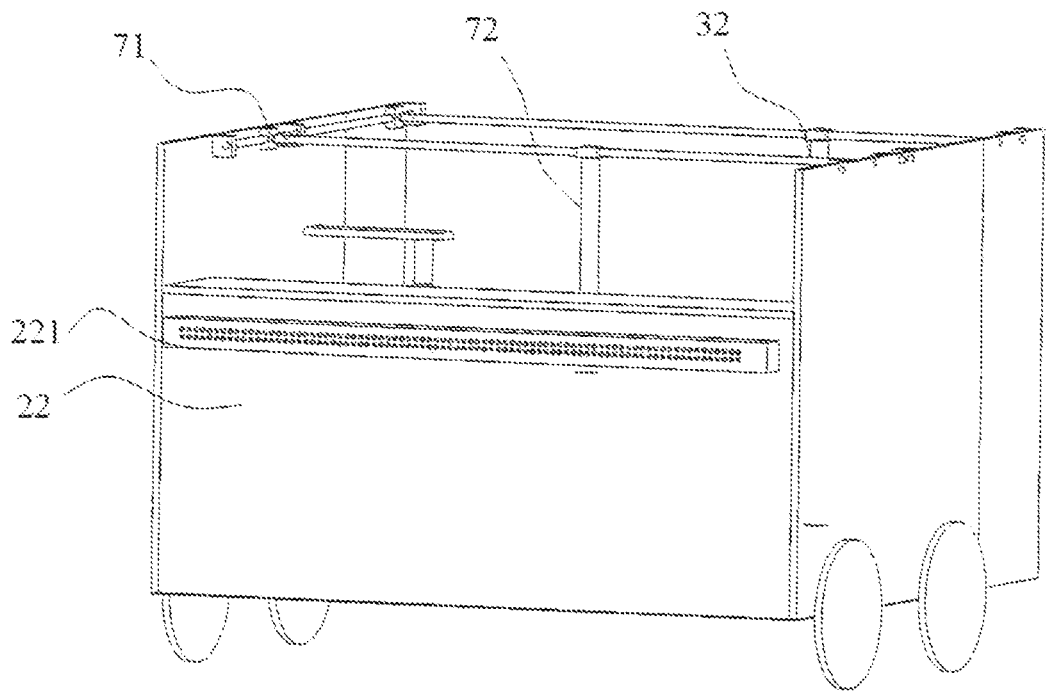
Figure 4:
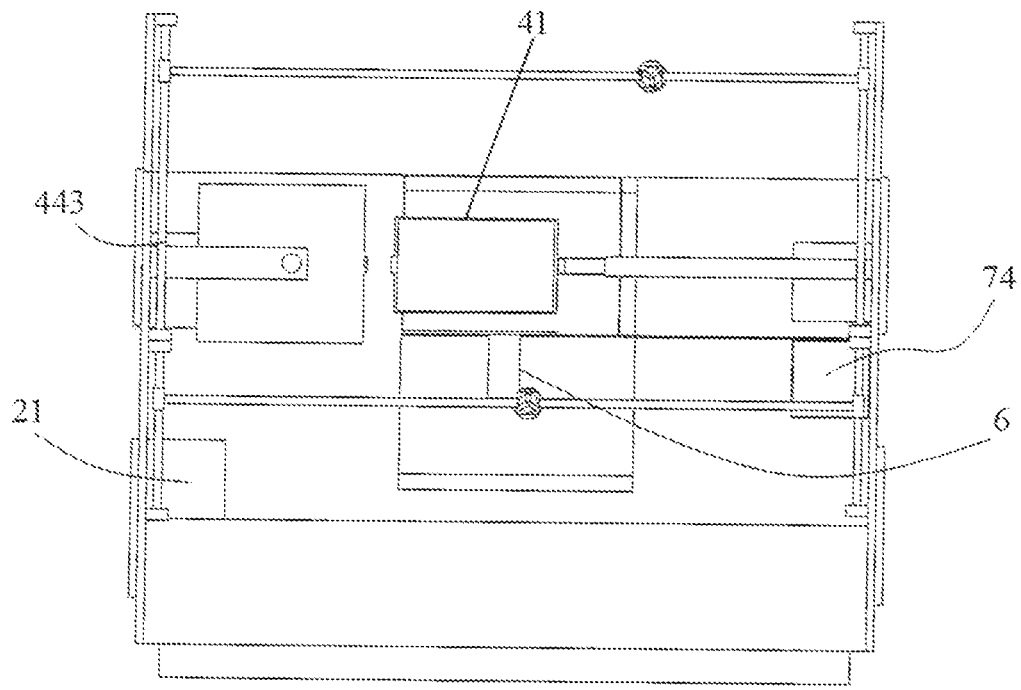
Figure 5:
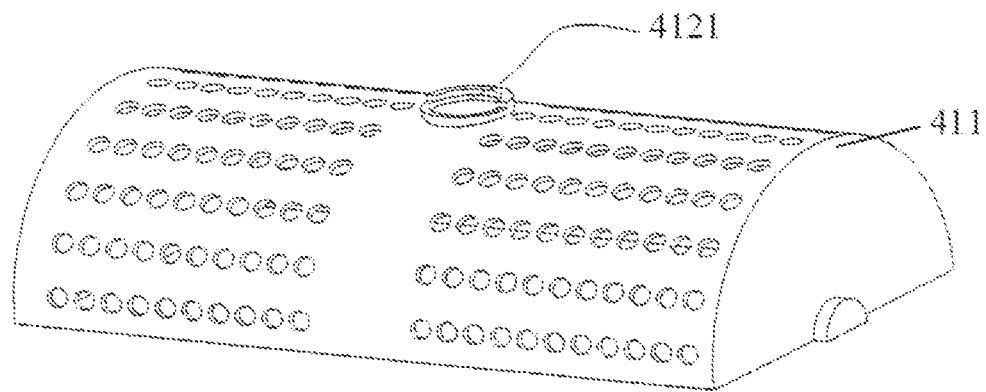
Figure 6:
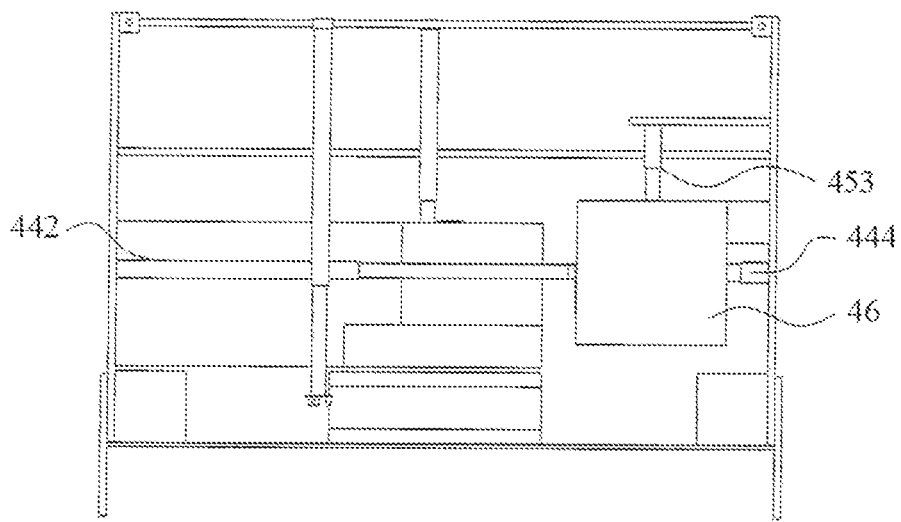
Figure 7:
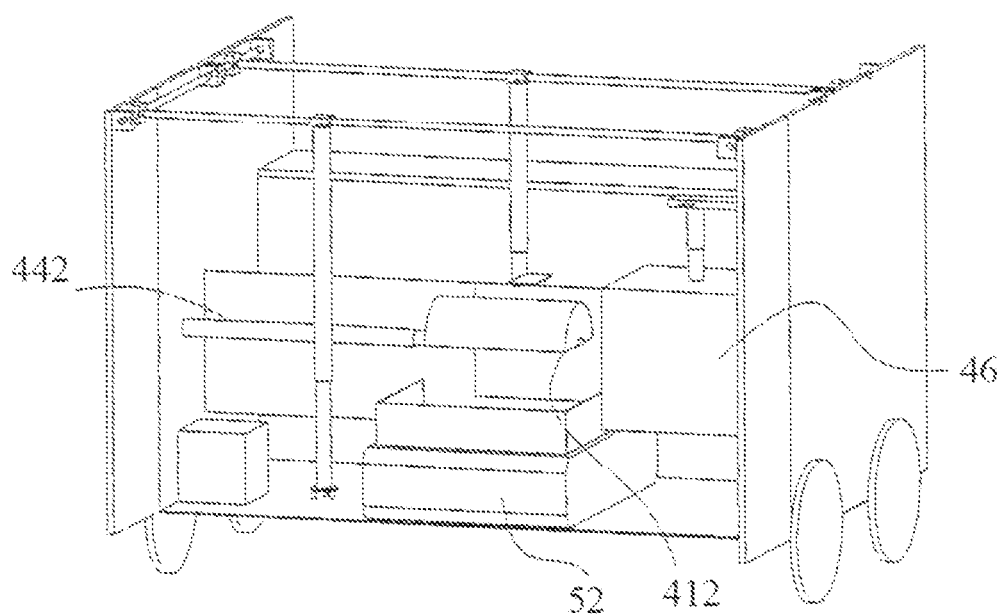

FIG. 1 is an overall block diagram of the invention;
FIG. 2 is a front view of the overall structure of the invention;
FIG. 3 is a rear view of the overall structure of the invention;
FIG. 4 is a top view of the overall structure of the invention;
FIG. 5 is a structural diagram of a sifting barrel of the invention;
FIG. 6 is a structural diagram of a sifting device of the invention;
FIG. 7 is a structural diagram of a sorting device of the invention.

Reference signs: 1, controller; 2, water sprinkling device; 21, water pump; 22, water tank; 221, water outlet; 3, soil grabbing device; 31, screw motor; 32, push-rod motor; 33, mechanical gripper; 4, sifting device; 41, sifting barrel; 411, upper sifting barrel; 412, lower sifting barrel; 4121, clamping groove; 42, drying plate; 441, rotating motor; 442, left push-rod motor; 443, fixing ring; 444, right push-rod motor; 451, fixing plate; 452, rotating motor; 453, push-rod motor; 454, semicircular clamping block; 46, recovery box; 51, shield plate; 52, conveying belt; 6, recognition device; 7, sorting device; 71, screw motor; 72, push-rod motor; 74, processing box.

DETAILED DESCRIPTION OF THE INVENTION

An automatic detection and recovery device for residual agricultural mulch films comprises a quadcopter 1, a wheeled motor 9 and a host computer 8. The quadcopter is provided with a controller, a near infrared water content analyzer and a WIFI module. As shown in FIG. 3, the wheeled robot comprises a water sprinkling device 2, a soil grabbing device 3, a sifting device 4, a delivery device 5, a recognition device 6, and a sorting device 7. The host computer 8 is used for information processing and interaction.

The water sprinkling device comprises a water pump and a water tank that are disposed behind the wheeled robot, wherein water is pumped out of the water tank by the water pump and is uniformly sprinkled via mesh-like outlets, and when the wheeled robot advances in a field, water is ceaselessly and uniformly sprinkled on the surface of the field;

The soil grabbing device comprises a three-degree-of-freedom motor for joint control, wherein the three-degree-of-freedom motor includes two screw motors and a push-rod motor, a mechanical gripper is used for grabbing and is mounted at a front end of the push-rod motor that is perpendicular to the ground so that the mechanical gripper is able to stretch and retreat perpendicular to the ground, a tail end of the push-rod motor is vertically mounted on a nut of one screw motor that is parallel to the ground, and one end of a screw of this screw motor is vertically mounted on a nut of the other screw motor that parallel to the ground, so that the mechanical gripper is able to move horizontally parallel to the ground; the soil grabbing device is disposed in front of the wheeled robot, and when the wheeled robot travels to a point where a residual mulch film is present, the soil grabbing device grabs soil at this point;

The sifting device comprises a sifting barrel, a drying plate, a pushing device, a rotating device, a moving device and a recovery box, wherein the sifting barrel is divided into an upper sifting barrel and a lower sifting barrel that are both hollow semi-cylinders; small round holes are formed all over the cylindrical surface of the upper sifting barrel, a clamping groove is formed in the center of the outer surface of the upper sifting barrel, an upper opening of the upper sifting barrel is in the shape of a hollow semicircular ring, semicircular bumps are disposed at the center of two ends of the upper sifting barrel, and the upper sifting barrel is always located in the recovery box; the surface of the lower sifting barrel is completely sealed, semicircular bumps are disposed at the center of two ends of the lower sifting barrel, and the bump at one end of the lower sifting barrel is connected to the pushing device; soil grabbed by the soil grabbing device is placed into the lower sifting barrel; the drying plate is mounted on one side of the recovery box and is used for drying the grabbed soil; the pushing device is a push-rod motor, a motor base is mounted on the rotating device, and the head of a push rod is connected to the lower sifting barrel to deliver the lower sifting barrel into the recovery box or extract the lower sifting barrel from the recovery box; the rotating device comprises a rotating motor, a push-rod motor and a fixing ring, wherein the rotating motor is located on one side of the recovery box and is provided with a rotating shaft vertically connected to a base of the pushing device, the push-rod motor is located on the other side of the recovery box, the fixing ring is mounted at the head of a push rod of the push-rod motor, the rotating device locks the circular bump at one end of the sifting barrel through the fixing ring, and the rotating motor drives the lower sifting barrel to rotate, so that soil in the sifting barrel is sifted out via the small holes in the surface of the upper sifting barrel; the moving device comprises a fixing plate, a rotating motor, a push-rod motor and a semicircular clamping block, a tail end of the rotating motor is fixed to the fixing plate, a rotating shaft of the rotating motor is connected to a tail end of the push-rod motor, the semicircular clamping block is drilled at the head of a push rod and is able to rise or fall and rotate; the recovery box is a hollow cuboid, round notches are formed in two end faces of the recovery box to allow the sifting barrel to enter or come out, and the round notch in the upper end face of the recovery box allows the push rod of the push-rod motor of the moving device to move;

The delivery device comprises a shield plate and a conveying belt, wherein the conveying belt is used for conveying residues left after sifting, and the shield plate is used for flatly spreading the residues in the conveying process;

The recognition device adopts a monocular camera, shoots the residues in real time, and sends photos to the host computer, and the host computer processes image data and then selects out weak pixels to determine a residual mulch film;

The sorting device comprises a three-degree-of-freedom motor, a mechanical gripper and a residual film recovery box, wherein the motor and the mechanical gripper are mounted in a manner similar to the motor and mechanical gripper of the soil grabbing device, and the mechanical gripper moves to and grabs the determined residual mulch film, and then places the grabbed residual mulch film into the recovery box.

The drying plate of the sifting device is mounted on the shield plate of the delivery device.

The upper sifting barrel of the sifting device is always located in the recovery box, and the moving device rotates by 180° in the clamping groove above the sifting barrel through the semicircular clamping block and then rises to be separated from the upper sifting barrel.

A semi-ring is disposed at a joint of the lower sifting barrel of the sifting device and the pushing device and is used for fixing the whole sifting barrel after the lower sifting barrel is conveyed back into the recovery box and is aligned with the upper sifting barrel, such that the sifting barrel can rotate smoothly;

A method of using the automatic detection and recovery device for residual agricultural mulch films comprises the following steps:

S1: planning a motion path of the wheeled robot according to the geometrical shape and position of a detected field, and uniformly sprinkling water into the defected field by the wheeled robot;

S2: after the water infiltrates into soil by a certain depth, detecting the water content of the detected field by the quadcopter carrying the near infrared water content analyzer along the motion path of the wheeled robot, determining a point where the water content of soil is high as a point where a residual mulch film is present by judging the water content of the soil, and recording the coordinates of this point;

S3: transmitting, by the quadcopter, the coordinates of the point where the residual mulch film is present to the wheeled robot, enabling the wheeled robot to sequentially move to the point where the residual mulch film is present along a planned path, and grabbing a soil mixture at this point;

S4: drying the soil mixture by the wheeled robot, and separating and recovering soil through high-speed rotation after drying; and S5: flatly spreading residues left after the soil is sifted, recognizing the residual mulch film by means of machine vision, and grabbing the residual mulch film by the mechanical gripper.

In operation:

The wheeled robot advances along a planned path, in this process, the water pump 21 pumps water from the water tank 22, and the water is discharged via the mesh-like outlets 221 to be uniformly sprinkled in the field; a period of time later after the water infiltrates into soil, the quadcopter flies along a planned path, the near infrared water content analyzer carried by the quadcopter detects the water content of the field, a point where the water content is high is determined as a point where a residual mulch film is present, and the coordinate position of the point where the residual mulch film is present is recorded and transmitted to the controller of the wheeled robot;

The wheeled robot sequentially advances to reach the point where the residual mulch film is present, the soil grabbing device 3 controls the two-degree-of-freedom screw motor 31 to enable the mechanical gripper 33 to move horizontally, the push-rod motor 32 stretches or retreats to enable the mechanical gripper 33 to move vertically, and when reaching the point where the residual mulch film is present, the mechanical gripper 33 grabs a soil mixture at this point and places it into the lower sifting barrel 412; after soil mixtures at all points where residual mulch films are present are grabbed, the soil grabbing process ends, and the drying plate 42 works for a period of time to dry the soil mixtures in the lower sifting barrel 412;

The left push-rod motor 442 stretches to convey the lower sifting barrel 412 into the recovery box 46; after the upper sifting barrel 411 and the lower sifting barrel 412 are aligned, one end of the sifting barrel 41 is fixed, the left push-rod motor 422 is stretched, and the other end of the sifting barrel 41 is fixed by the fixing ring at the head of the push rod of the left push-rod motor 422; after the rotating motor of the moving device rotates by 180°, the left push-rod motor 422 retreats, and at this moment, the semicircular clamping block 454 is separated from the upper sifting barrel 411, so that the upper sifting barrel 411 is separated from the moving device; the rotating motor 441 starts to rotate and drives the sifting barrel 41 to rotate in the recovery box 46, in this process, soil in the soil mixtures is separated into the recovery box 46 via the small holes in the surface of the upper sifting barrel 411, and residues such as residual mulch films, stones and rootstocks are left in the sifting barrel 41;

As shown in FIG. 5, after the sifting barrel 41 rotates to the initial state, the push-rod motor 453 of the moving device stretches to enable the semicircular clamping block 454 to abut against the bottom of the clamping groove in the upper sifting barrel 411, at this moment, the push-rod motor 453 stops stretching, the rotating motor 452 works to drive the semicircular clamping block 454 to rotate to connect the upper sifting barrel 411 and the moving device, and the left push-rod motor 422 retreats to drive the lower sifting barrel 412 to be extracted from the recovery box 46; when the lower sifting barrel 412 is entirely located over the conveying belt 52, the left push-rod motor 422 stops working, the rotating motor 441 rotates by 180° to place the residues in the lower sifting barrel 412 onto the conveying belt 52, and then the conveying belt 52 rotates to drive the residues thereon to move; in the moving process of the residues, the shield plate 51 located above the conveying belt by a certain distance flatly spreads the residues, and the conveying belt stops rotating when conveying the residues to an area where the recognition device 6 is located; the recognition device takes a picture of the residues and transmits the picture to the host computer, and the host computer detects the brightness values of all positions of the picture, determines points with high brightness values as points where residual mulch films are present, and transmits coordinate positions of the residual mulch films to the controller 1 of the wheeled robot; the controller 1 controls the screw motor 71 and the push-rod motor 72 to drive the mechanical gripper to reach the positions where the residual mulch films are located to grab the residual mulch films and place the grabbed residual mulch films into the processing box 74, so that the recovery process of the residual mulch films is completed.

What is claimed is:

1. An automatic detection and recovery device for residual agricultural mulch film comprises a quadcopter, a wheeled robot and a host computer; the quadcopter includes a controller, a near infrared water content analyzer and a WIFI module; the wheeled robot comprises a water sprinkling device, a soil grabbing device, a sifting device, a delivery device, a recognition device, and a sorting device;
   the water sprinkling device comprises a water pump and a water tank that are behind the wheeled robot, wherein water is pumped out of the water tank by the water pump and is uniformly sprinkled via mesh-like outlets, and when the wheeled robot advances in a field, water is ceaselessly and uniformly sprinkled on the surface of the field;
   the soil grabbing device comprises a mechanical gripper and a three-degree-of-freedom motor for joint control, wherein the three-degree-of-freedom motor includes first and second screw motors and a push-rod motor, the mechanical gripper is used for grabbing and is mounted at a front end of the push-rod motor that is perpendicular to the ground so that the mechanical gripper is able to stretch and retreat perpendicular to the ground, a tail end of the push-rod motor is vertically mounted on a nut of the first screw motor that is parallel to the ground, and one end of a screw of said first screw motor is vertically mounted on a nut of the second screw motor that parallel to the ground, so that the mechanical gripper is able to move horizontally parallel to the ground; the soil grabbing device is in front of the wheeled robot, and when the wheeled robot travels to a point where a residual mulch film is present, the soil grabbing device grabs soil at this point;
   the sifting device comprises a sifting barrel, a drying plate, a pushing device, a rotating device, a moving device and a recovery box, wherein the sifting barrel is divided into an upper sifting barrel and a lower sifting barrel that are both hollow semi-cylinders; the cylindrical surface of the upper sifting barrel includes small round holes all over said cylindrical surface, the center of the outer surface of the upper sifting barrel includes a clamping groove, an upper opening of the upper sifting barrel is a hollow semicircular ring, the center of two ends of the upper sifting barrel includes semicircular bumps, and the upper sifting barrel is always located in the recovery box; the surface of the lower sifting barrel is completely sealed, the center of two ends of the lower sifting barrel includes semicircular bumps, and the bump at one end of the lower sifting barrel is connected to the pushing device; soil grabbed by the soil grabbing device is placed into the lower sifting barrel; the drying plate is mounted on one side of the recovery box and is used for drying the grabbed soil; the pushing device is a push-rod motor, a motor base is mounted on the rotating device, and the head of a push rod is connected to the lower sifting barrel to deliver the lower sifting barrel into the recovery box or extract the lower sifting barrel from the recovery box; the rotating device comprises a rotating motor, a push-rod motor and a fixing ring, wherein the rotating motor is located on one side of the recovery box and includes a rotating shaft vertically connected to a base of the pushing device, the push-rod motor of the rotating device is located on the other side of the recovery box, the fixing ring is mounted at the head of a push rod of the push-rod motor of the rotating device, the rotating device locks the circular bump at one end of the sifting barrel through the fixing ring, and the rotating motor drives the lower sifting barrel to rotate, so that soil in the sifting barrel is sifted out via the small holes in the surface of the upper sifting barrel; the moving device comprises a fixing plate, a rotating motor, a push-rod motor of the rotating device and a semicircular clamping block, a tail end of the rotating motor is fixed to the fixing plate, a rotating shaft of the rotating motor is connected to a tail end of the push-rod motor, the semicircular clamping block is drilled at the head of a push rod and is able to rise or fall and rotate; the recovery box is a hollow cuboid, the recovery box includes two end faces having round notches, wherein the round notches allow the sifting barrel to enter or come out, and the round notch in the upper end face of the recovery box allows the push rod of the push-rod motor of the moving device to move;
   the delivery device comprises a shield plate and a conveying belt, wherein the conveying belt is used for conveying residues left after sifting, and the shield plate is used for flatly spreading the residues in the conveying process;
   the recognition device has a monocular camera, shoots the residues in real time, and sends photos to the host computer, and the host computer processes image data and then selects out weak pixels to determine a residual mulch film;
   the sorting device comprises a three-degree-of-freedom motor, a mechanical gripper and a residual film recovery box, wherein the motor and the mechanical gripper of the sorting device are mounted in a manner similar to the motor and mechanical gripper of the soil grabbing device, and the mechanical gripper of the sorting device moves to and grabs the determined residual mulch film, and then places the grabbed residual mulch film into the recovery box.

2. The automatic detection and recovery device for residual agricultural mulch films according to claim 1, wherein the drying plate of the sifting device is mounted on the shield plate of the delivery device.

3. The automatic detection and recovery device for residual agricultural mulch film according to claim 1, wherein the upper sifting barrel of the sifting device is always located in the recovery box, and the moving device rotates by 180° in the clamping groove above the sifting barrel through the semicircular clamping block and then rises to be separated from the upper sifting barrel.

4. The automatic detection and recovery device for residual agricultural mulch film according to claim 1, wherein a semi-ring at a joint of the lower sifting barrel of the sifting device and the pushing device and is used for fixing the whole sifting barrel after the lower sifting barrel is conveyed back into the recovery box and is aligned with the upper sifting barrel, such that the sifting barrel can rotate smoothly.

5. A method of using the automatic detection and recovery device for residual agricultural mulch film according to claim 1 comprises the following steps:
- S1: planning a motion path of the wheeled robot according to the geometrical shape and position of a detected field, and uniformly sprinkling water into the defected field by the wheeled robot;
- S2: after the water infiltrates into soil by a certain depth, detecting the water content of the detected field by the quadcopter carrying the near infrared water content analyzer along the motion path of the wheeled robot, determining a point where the water content of soil is high as a point where a residual mulch film is present by judging the water content of the soil, and recording the coordinates of this point;
- S3: transmitting, by the quadcopter, the coordinates of the point where the residual mulch film is present to the wheeled robot, enabling the wheeled robot to sequentially move to the point where the residual mulch film is present along a planned path, and grabbing a soil mixture at this point;
- S4: drying the soil mixture by the wheeled robot, and separating and recovering soil through high-speed rotation after drying;
- S5: flatly spreading residues left after the soil is sifted, recognizing the residual mulch film by means of machine vision, and grabbing the residual mulch film by the mechanical gripper of the soil grabbing device.

* * * * *